(12) United States Patent
Boese et al.

(10) Patent No.: US 7,916,827 B2
(45) Date of Patent: Mar. 29, 2011

(54) METHOD FOR EVALUATING PROJECTION DATASETS OF AN OBJECT UNDERGOING EXAMINATION

(75) Inventors: Jan Boese, Eckental (DE); Günter Lauritsch, Erlangen (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 694 days.

(21) Appl. No.: 11/824,456

(22) Filed: Jun. 29, 2007

(65) Prior Publication Data

US 2008/0013675 A1 Jan. 17, 2008

(30) Foreign Application Priority Data

Jun. 30, 2006 (DE) .................. 10 2006 030 811

(51) Int. Cl.
A61B 6/03 (2006.01)
(52) U.S. Cl. ............... 378/4; 378/8; 378/51; 378/901
(58) Field of Classification Search ............ 378/4, 8, 378/51, 901; 382/131
See application file for complete search history.

(56) References Cited

U.S. PATENT DOCUMENTS

| | | | | |
|---|---|---|---|---|
| 6,435,714 | B1* | 8/2002 | Bruder | 378/196 |
| 6,529,575 | B1* | 3/2003 | Hsieh | 378/4 |
| 6,909,769 | B2 | 6/2005 | Bruder et al. | |
| 2006/0120507 | A1* | 6/2006 | Brunner et al. | 378/62 |
| 2007/0030945 | A1 | 2/2007 | Boese et al. | |
| 2007/0104309 | A1* | 5/2007 | Schonborn et al. | 378/4 |

FOREIGN PATENT DOCUMENTS

| | | |
|---|---|---|
| DE | 101 19 228 A1 | 12/2002 |
| DE | 10 2005 016 472 A1 | 10/2006 |
| WO | WO 2006/003578 A1 | 1/2006 |

OTHER PUBLICATIONS

Montes et al., Analysis of Time Resolution in Dynamic Computed Tomography for Perfusion Studies, 2004 IEEE Nuclear Science Symposium Conference Record, vol. 7, pp. 4195-4199.*
Lauritsch et al., Toward Cardiac Angiographic Computed Tomography, 2005 IEEE Nuclear Science Symposium Record, vol. 4, pp. 2350-2354.*
Kurp, Axiom Artis FD Systems, DynaCT—A breakthrough in Interventional 3D Imaging, Jan. 2005, Reprint from Medical Solutions, Siemens Medical, pp. 46-51.*
M. Grass, T. Köhler, R. Proksa; "3D Cone-Beam CT Reconstruction for Circular Trajectories"; Phys. Med. Biol.; 2000; pp. 329-347; vol. 45; IOP Publishing Ltd.

(Continued)

*Primary Examiner* — Edward J Glick
*Assistant Examiner* — John M Corbett

(57) ABSTRACT

The invention relates to a method for evaluating projection datasets of an object undergoing examination. Each projection dataset is assigned a swiveling angle and a recording instant. Each data element of each projection dataset defines a projection line along which an X-ray beam has traveled from an X-ray source to an X-ray detector. The projection datasets form recording groups each of which corresponds with the projection datasets that were recorded during a single swiveling action. A computer determines reconstruction datasets using the projection datasets. Each reconstruction dataset contains at least one reconstruction data value assigned to a reconstruction line. Using a temporal interpolation, the computer determines the reconstruction datasets in such a way that they refer to a uniform reconstruction time. The computer determines a reconstruction of the object undergoing examination using the reconstruction datasets.

20 Claims, 11 Drawing Sheets

OTHER PUBLICATIONS

Pau Montes and Günter Lauritsch; "Noise Reduction by Temporal Estimation in Perfusion Computer Tomography"; submitted to IEEE Nuclear Science Symposium Wyndham El Conquistador Resort; Puerto Rico; Oct. 23-29, 2005; pp. 1-2.

Pau Montes and Günter Lauritsch; "Analysis of Time Resolution in Dynamic Computed Tomography for Perfusion Studies"; Submitted to IEEE Transactions on Nuclear Science; Oct. 16-22, 2004; pp. 1-12.

* cited by examiner

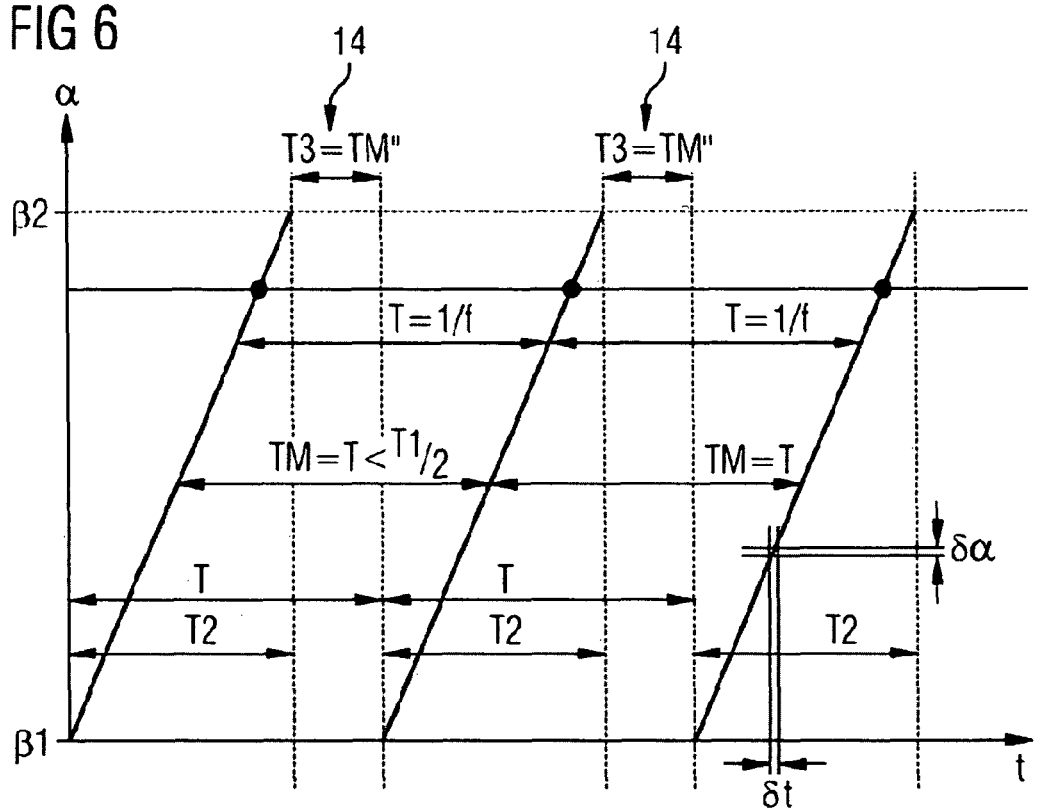
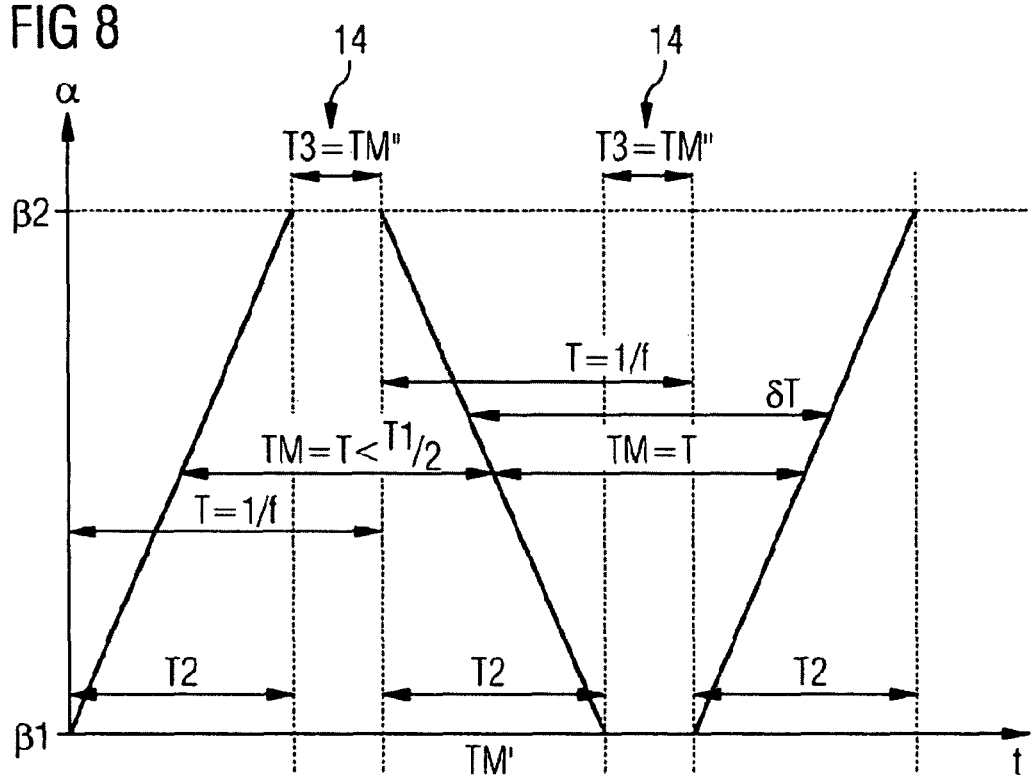

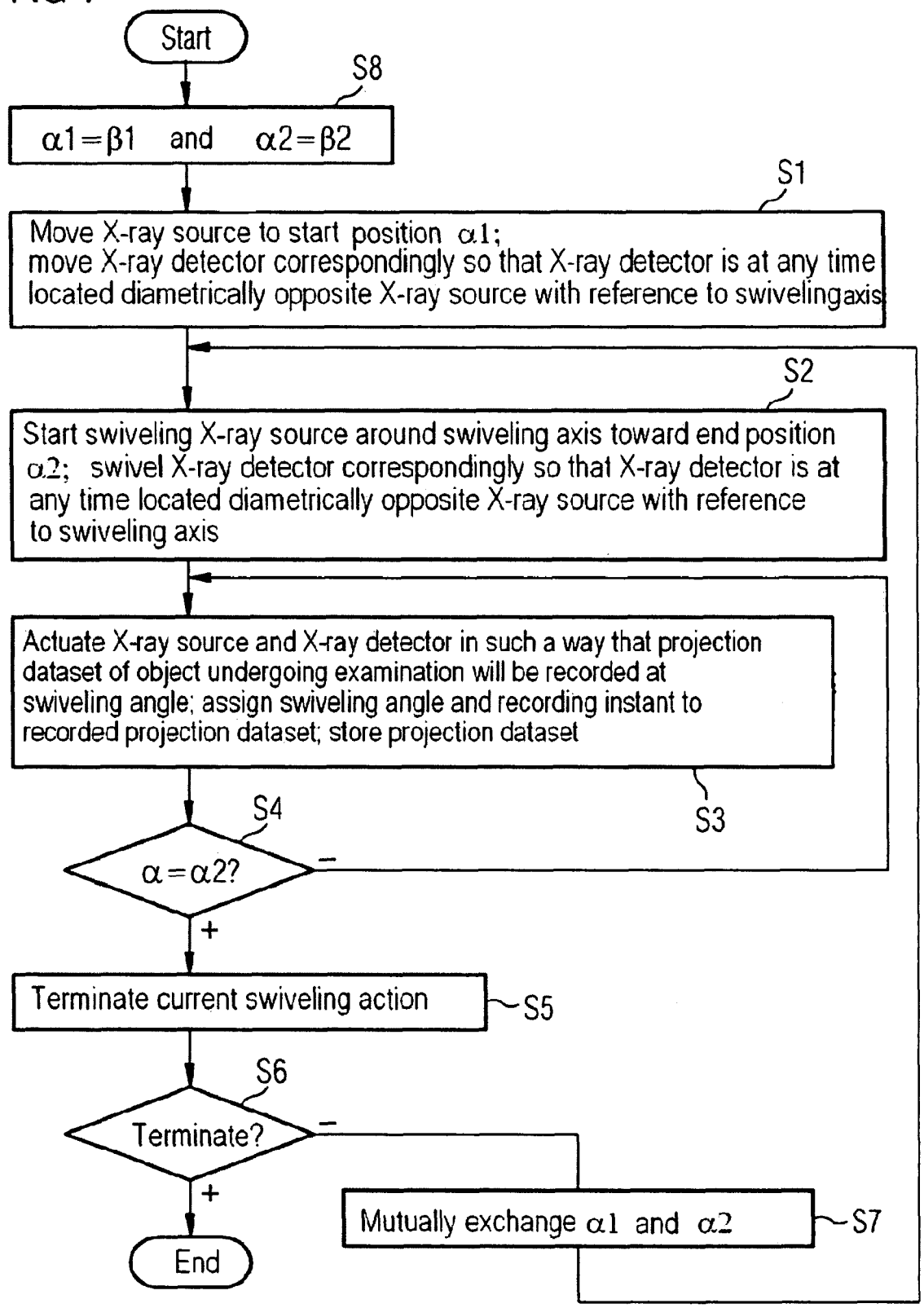

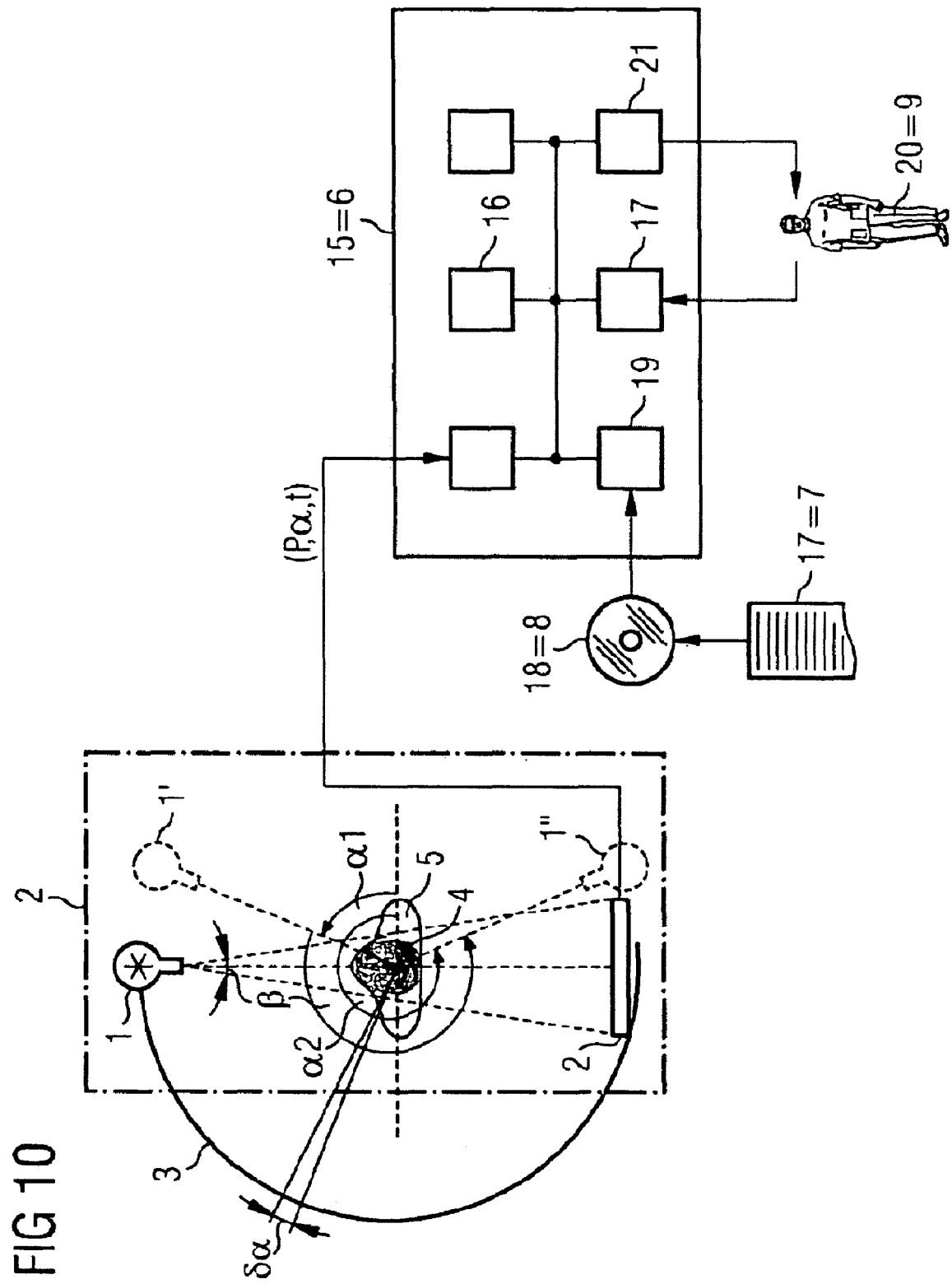

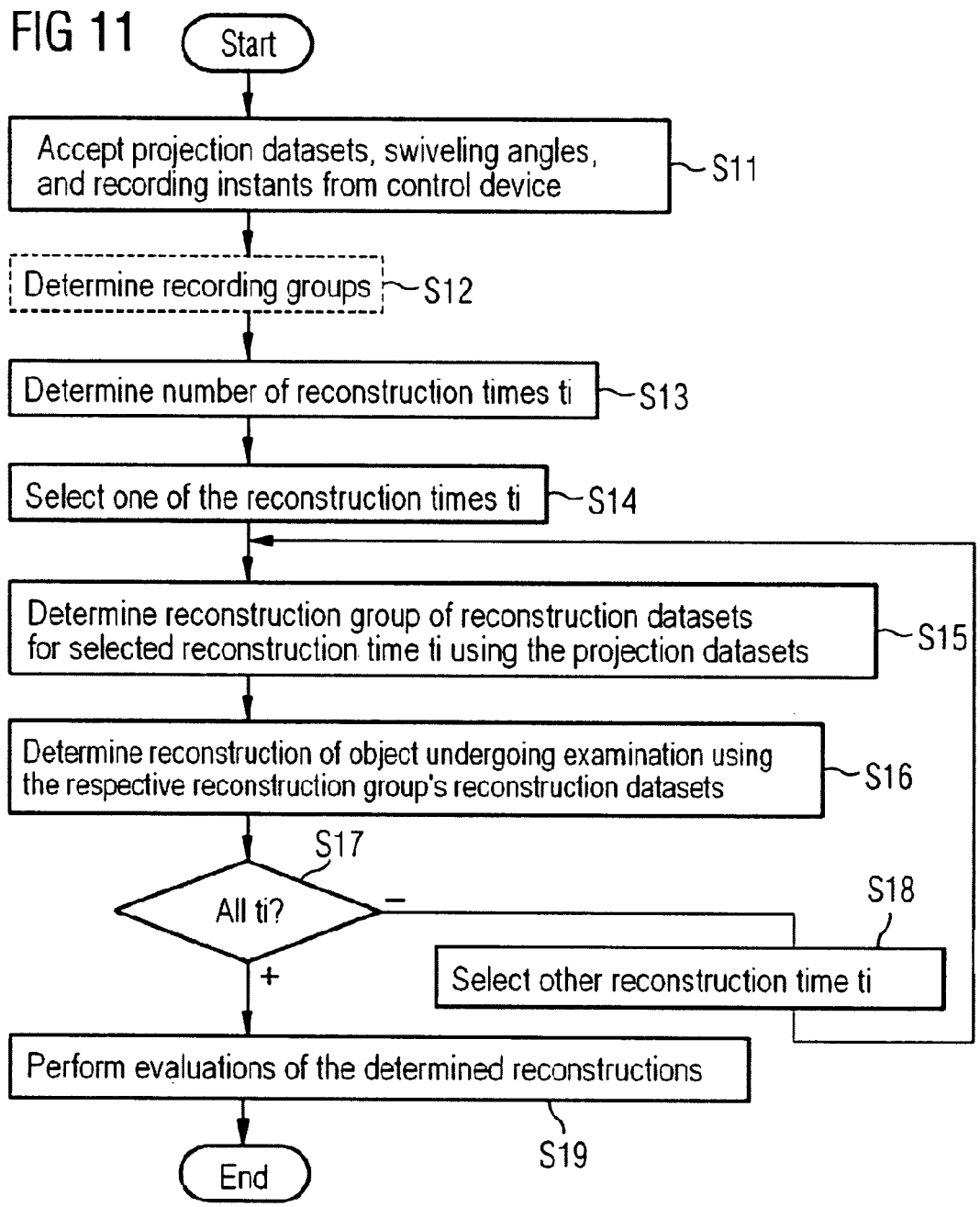
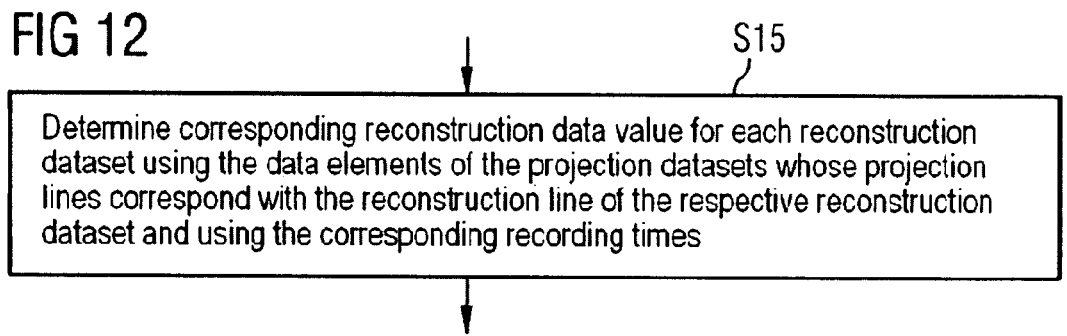

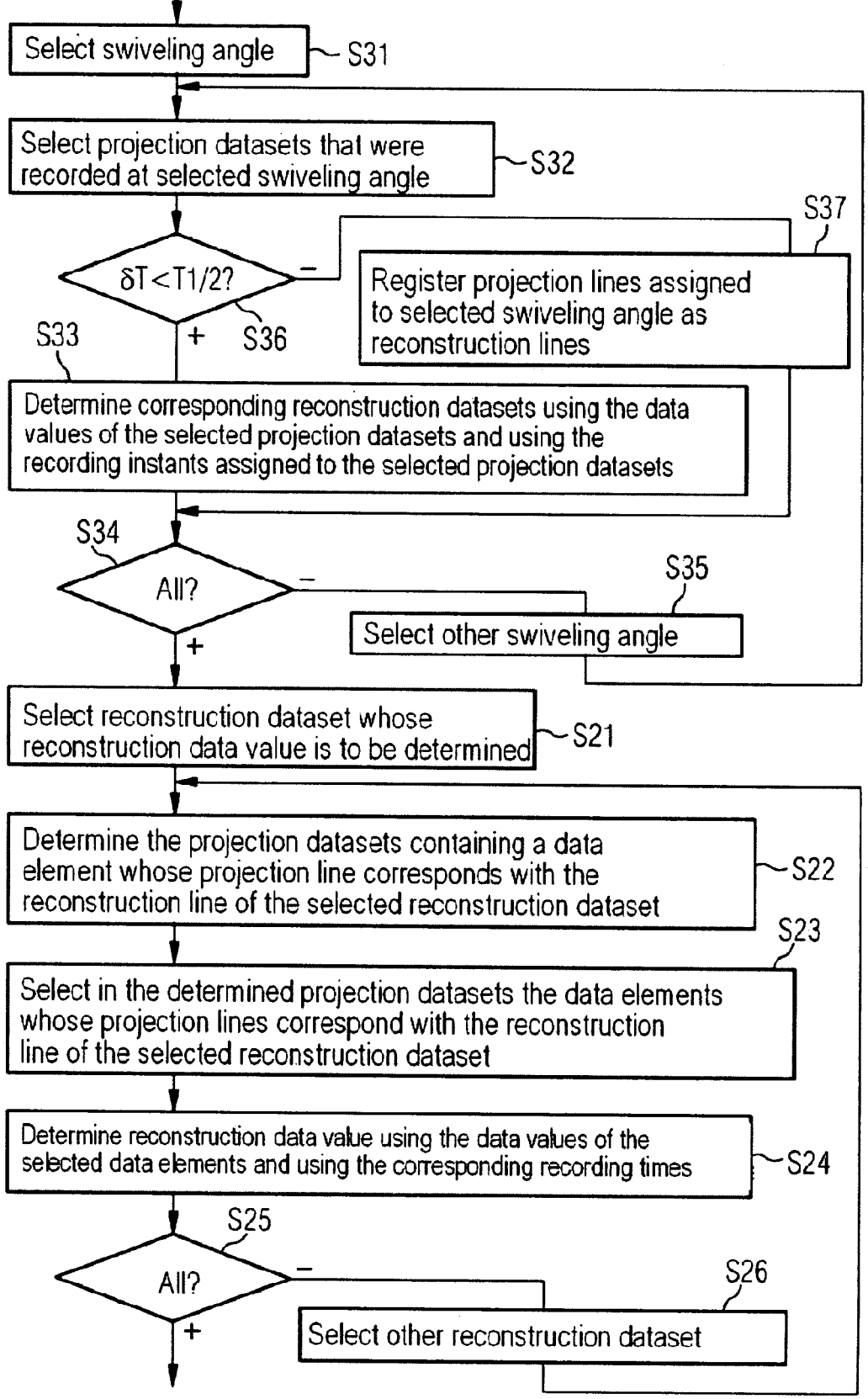

METHOD FOR EVALUATING PROJECTION DATASETS OF AN OBJECT UNDERGOING EXAMINATION

CROSS REFERENCE TO RELATED APPLICATIONS

This application claims priority of German application No. 10 2006 030 811.5 filed Jun. 30, 2006, which is incorporated by reference herein in its entirety.

FIELD OF THE INVENTION

The present invention relates to a method for evaluating projection datasets of an object undergoing examination.

BACKGROUND OF THE INVENTION

Methods for evaluating projection datasets of an object undergoing examination and the methods for acquiring such projection datasets are generally known. One-dimensional or two-dimensional projection datasets of the object undergoing examination are acquired by means of the acquisition methods. A two-dimensional or three-dimensional reconstruction of the object undergoing examination is as a rule determined by means of the evaluating methods. The reconstruction is evaluated further. Evaluating can be performed automatically by a computer. It is alternatively or additionally possible for (in the case of a two-dimensional reconstruction) the reconstruction itself or, as the case may be (in the case of a three-dimensional reconstruction), two-dimensional representations of the reconstruction to be fed out to a user (usually a doctor) on a display device.

The acquisition methods and the corresponding evaluating methods are differentiated according to multifarious criteria. The kind of signal carrier, for example ultrasound, magnetic resonance, or X-rays, can be cited as the first differentiating criterion.

The acquisition methods and the evaluating methods are further differentiated according to the nature of their subsequent evaluating. For example the object undergoing examination is to be reconstructed using the projection datasets. This limitation usually requires the object undergoing examination to within the scope of the acquisition method be located within the range of a swiveling axis, an X-ray source to be swiveled around the swiveling axis, an X-ray detector to be swiveled correspondingly while the X-ray source is being swiveled so that the X-ray detector will at any time be located diametrically opposite the X-ray source with reference to the swiveling axis, and in each case one of the projection datasets to be recorded through appropriately actuating the X-ray source and X-ray detector at swiveling angles of the X-ray source and stored. The respective swiveling angle is assigned to the respective projection dataset. A recording instant at which the respective projection dataset was recorded is generally also assigned to the respective projection dataset. The angular range through which the X-ray source is swiveled is as a rule greater than 180°. A typical angular range is, for example, 200°, 220°, or 270°.

The acquisition methods and corresponding evaluating methods are further differentiated according to the nature of the object undergoing examination. For instance there are objects undergoing examination that are static. In that case it will suffice for the X-ray source to execute a single swiveling action around the swiveling axis. The time required for swiveling is not critical. The projection datasets can in the case of said kind of individual embodiments be acquired by means of, for instance, a CT system or C-arm X-ray system.

It is alternatively possible for the object undergoing examination to move, in particular iteratively. A typical instance of an iteratively moving object undergoing examination is the human heart. A CT system is as a rule used for performing the acquisition method in the case of said type of objects undergoing examination. The reason is that in CT systems the X-ray source rotates around the swiveling axis at a rotational speed of 75 rev/min and more. Rotational speeds of 120 to 180 rev/min are even possible with CT systems of more modern design. So the X-ray source rotates much faster in CT systems than in C-arm systems, which—depending on the specific embodiment—require at least three seconds for the X-ray source to swivel once through approximately 200° to 220°. The angular range (180° or more) required for determining the reconstruction can therefore be traversed in a much shorter time using a CT scanner than when a C-arm system is used.

Described in the older German patent application 10 2005 016 472.2 is a possibility based on which a C-arm X-ray system can be employed for acquiring the projection datasets of the object undergoing examination although the object undergoing examination moves iteratively. Said patent application was still unpublished prior to the application date of the present invention. It therefore does not constitute a general state of the art but simply has to be considered as part of the examination for novelty within the German patenting process.

A plurality of swiveling actions are performed according to the disclosure in DE 10 2005 016 472.2. With reference to each recorded projection dataset, phase information about the object undergoing examination is additionally recorded and assigned to the respective projection dataset.

It is furthermore possible for the object undergoing examination neither to be purely static nor to move rapidly iteratively, but nonetheless to change relatively slowly. A typical example of an object of said type undergoing examination is the human brain when an injected contrast medium gradually spreads within the brain. Long time series of projection datasets are recorded in such cases, for example over a period of from 30 seconds to 1 minute.

CT scanners are predominantly employed in the prior art for recording projection datasets of said type. Reference is made by way of example to the technical articles "Noise Reduction by Temporal Estimation in Perision Computed Tomography" by P. Montes and G. Lauritsch, IEEE Nuclear Science Symposium Conference Record, Oct. 23-29, 2005, Wyndham El Conquistador Resort, Puerto Rico, and "Analysis of Time Resolution in Dynamic Computed Tomography for Perfusion Studies", also by P. Montes and G. Lauritsch, IEEE Nuclear Science Symposium Conference Record, Oct. 16-22, 2004, Rome, Italy.

With the last-cited procedure a sequence of reconstructions is determined using the time series of projection datasets. Important physiological parameters relating to the supply of blood to human tissue can be determined using the sequence of reconstructions. Examples of such parameters are the volume of blood, blood flow, permeability etc. The methods have recently become established and are being applied in practice. They are, though, owing to the spatial limitations of CT systems restricted to the diagnostic sphere. They cannot be used in the interventional sphere.

C-arm X-ray systems allow far better access to the object undergoing examination. They are therefore employed not only in the diagnostic sphere but also in the interventional sphere. However, they are as a rule used only for image recording as such.

A method for evaluating datasets of an object undergoing examination is known from WO 2006/003578 A1. Each projection dataset is assigned a recording instant at which the respective projection dataset was recorded by an X-ray detector located diametrically opposite an X-ray source with reference to a swiveling axis. Each projection dataset is furthermore assigned a swiveling angle through which the X-ray source had at the recording instant swiveled with reference to the swiveling axis. Together with the swiveling angle assigned to the respective projection dataset, each data element of each projection dataset defines a projection line along which an X-ray beam has traveled on its way from the X-ray source to the X-ray detector. The projection datasets are combined by the computer into recording groups. Each recording group extends in temporal terms from a starting instant to a finishing instant. The recording groups overlap in time. The computer determines a three-dimensional reconstruction of the object undergoing examination using the projection datasets of in each case one recording group. The respective reconstruction can refer to an instant corresponding with the mean between the starting instant and finishing instant.

SUMMARY OF THE INVENTION

The object of the present invention is to make a method available for evaluating projection datasets of an object undergoing examination on the basis of which datasets the quality of the reconstruction can be improved.

Said object is achieved by the claims.

The object undergoing examination is within the scope of the acquisition method located within the range of a swiveling axis. An X-ray source is swiveled around the swiveling axis during a plurality of mutually discrete swiveling actions. An X-ray detector is swiveled correspondingly during the X-ray source's swiveling actions so that the X-ray detector will at any time be located diametrically opposite the X-ray source with reference to the swiveling axis. In each case one of the projection datasets will be recorded through appropriately actuating the X-ray source and X-ray detector at swiveling angles of the X-ray source and stored. Each projection dataset will be assigned the respective swiveling angle and a recording instant at which the respective projection dataset was recorded. Together with the swiveling angle assigned to the respective projection dataset, each data element of each projection dataset will define a projection line along which an X-ray beam has traveled on its way from the X-ray source to the X-ray detector.

Within the scope of the inventive evaluating method the projection datasets form recording groups each of which corresponds with the projection datasets that were recorded during a single swiveling action of the X-ray source around the swiveling axis. A computer determines at least one reconstruction group of reconstruction datasets using the projection datasets. The reconstruction datasets constitute the input data on the basis of which the reconstruction of the object undergoing examination is determined. Each reconstruction dataset contains at least one reconstruction data value assigned to a reconstruction line. The computer determines each determined reconstruction group's reconstruction datasets in such a way that they refer to a reconstruction time that is uniform for the respective reconstruction group. Using each determined reconstruction group's reconstruction datasets it determines in each case one reconstruction group of the object undergoing examination. For each reconstruction dataset the computer determines the reconstruction data value using the data elements of the projection datasets whose projection lines correspond as far as possible with the reconstruction line and using the recording times assigned to the respective projection datasets through temporal interpolation.

Because each recording group corresponds with the projection datasets of a single swiveling action, the swiveling angles of the projection datasets assignable to the same recording group form a strictly monotonic function of the corresponding recording instants.

If the swiveling actions were in the same direction during recording, then the functions will exhibit the same monotony in all recording groups. A time distance between the temporally last projection dataset of a recording group and the temporally first projection dataset of the immediately following recording group will in that case be greater than a time distance between two projection datasets in direct succession within the same recording group.

If conversely, swiveling actions in direct succession were in opposite directions, then the functions will change their monotony from recording group to temporally immediately following recording group.

It is possible for the computer to determine the recording groups. The recording groups as such can alternatively have already been specified to the computer, or else determining of the recording groups can be omitted.

It is possible for the projection lines of each projection dataset to be oriented parallel to each other. The projection lines of each projection dataset can alternatively have a common intersecting point.

For determining the reconstruction data values the computer preferably uses only the data elements whose recording instants bracket the reconstruction time. In the simplest case the computer performs a linear interpolation. It is alternatively possible to use higher functions, in particular splines.

It is always possible for the computer to determine weighting factors defining the extent to which individual data elements of the projection lines each contribute to a corresponding reconstruction data value by reconstruction lines. It is, though, more efficient for the computer to determine the weighting factors exclusively or at least as far as possible by swiveling angles.

It is possible for the computer program to cause only the evaluating method to be performed. It is alternatively possible for the computer program additionally to be embodied as a control program for an X-ray system and cause the computer to control the X-ray system according to an acquisition method of the above-described type. The X-ray system's control device will in that case be identical to the computer.

BRIEF DESCRIPTION OF THE DRAWINGS

Further advantages and specifics will emerge from the following description of exemplary embodiments in conjunction with the schematic drawings:

FIG. 6 is a time chart,
FIG. 7 is a flowchart,
FIG. 8 is a time chart,
FIG. 10 is a block diagram of an X-ray system having a computer,
FIGS. 11 and 12 are flowcharts,
FIGS. 15 to 17 are flowcharts.

DETAILED DESCRIPTION OF THE INVENTION

Figure 1:
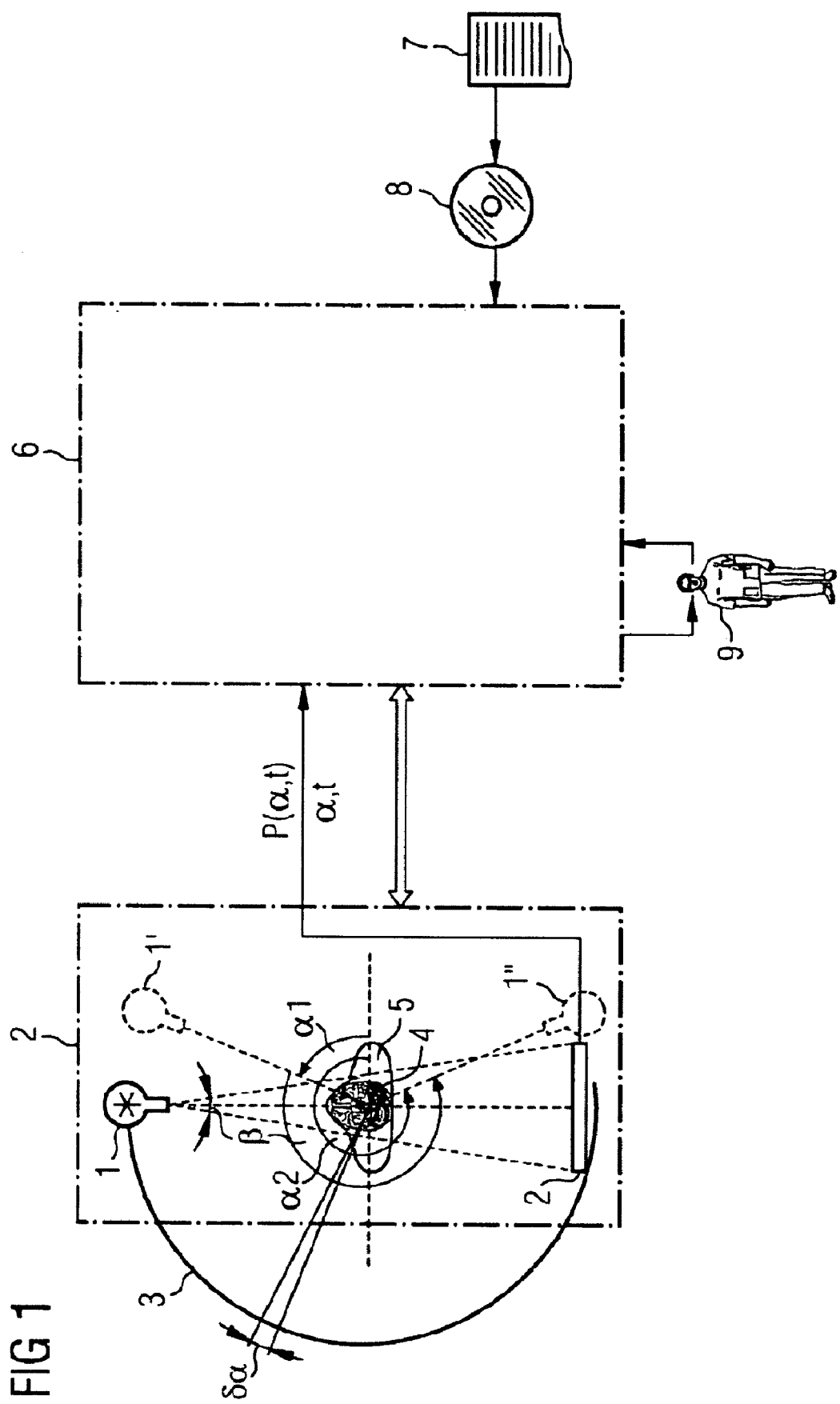
FIG. 1 is a block diagram of an X-ray system.

According to FIG. 1 an X-ray system has an X-ray source 1 and an X-ray detector 2. The X-ray source 1 and X-ray detector 2 are according to FIG. 1 located on a schematically indicated C-arm 3. The X-ray source 1 and X-ray detector 2 can be swiveled by means of a drive (not shown) around a common swiveling axis 4 so that the X-ray detector 2 will at any time be located diametrically opposite the X-ray source 1 with reference to the swiveling axis 4.

The X-ray system is owing to the presence of the C-arm 3 embodied as a C-arm X-ray system. It is, though, basically possible to use any embodiment of an X-ray system that makes the above-described swiveling action possible.

An object 5 undergoing examination is located within the range of the swiveling axis 4. For example a patient can by means of a patient table (not shown) be positioned in such a way that a desired part of the patient's body is located within the range of the swiveling axis 4. It is assumed below—purely by way of example—that the desired part of the body is a person's brain.

The person's brain 5 is a basically static organ. It does not move. The flow of blood therein basically also remains the same. If, though, a contrast medium is present in the person's blood then the object 5 undergoing examination will change over time because the contrast medium will first gradually be carried into the brain 5 then immediately washed out again. The change over time takes place at time constants within a range of several seconds. A minimum time constant T1 that corresponds with the fastest change over time is customarily within a range of approximately 10 seconds.

The X-ray source 1, the X-ray detector 2, the C-arm 3, and, where applicable, the patient table are controlled by means of a control device 6. The control device 6 is as a rule a programmable control device. It processes a control program 7 supplied to it via a data medium 8 on which the control program 7 is stored in exclusively machine-readable form. The control program 7 causes the control device 6 to accept control instructions from an operator 9. The control device 6 will when appropriate control instructions have been specified operate the X-ray system according to an acquisition method that will be explained in more detail below in conjunction with FIG. 2.

Figure 2:
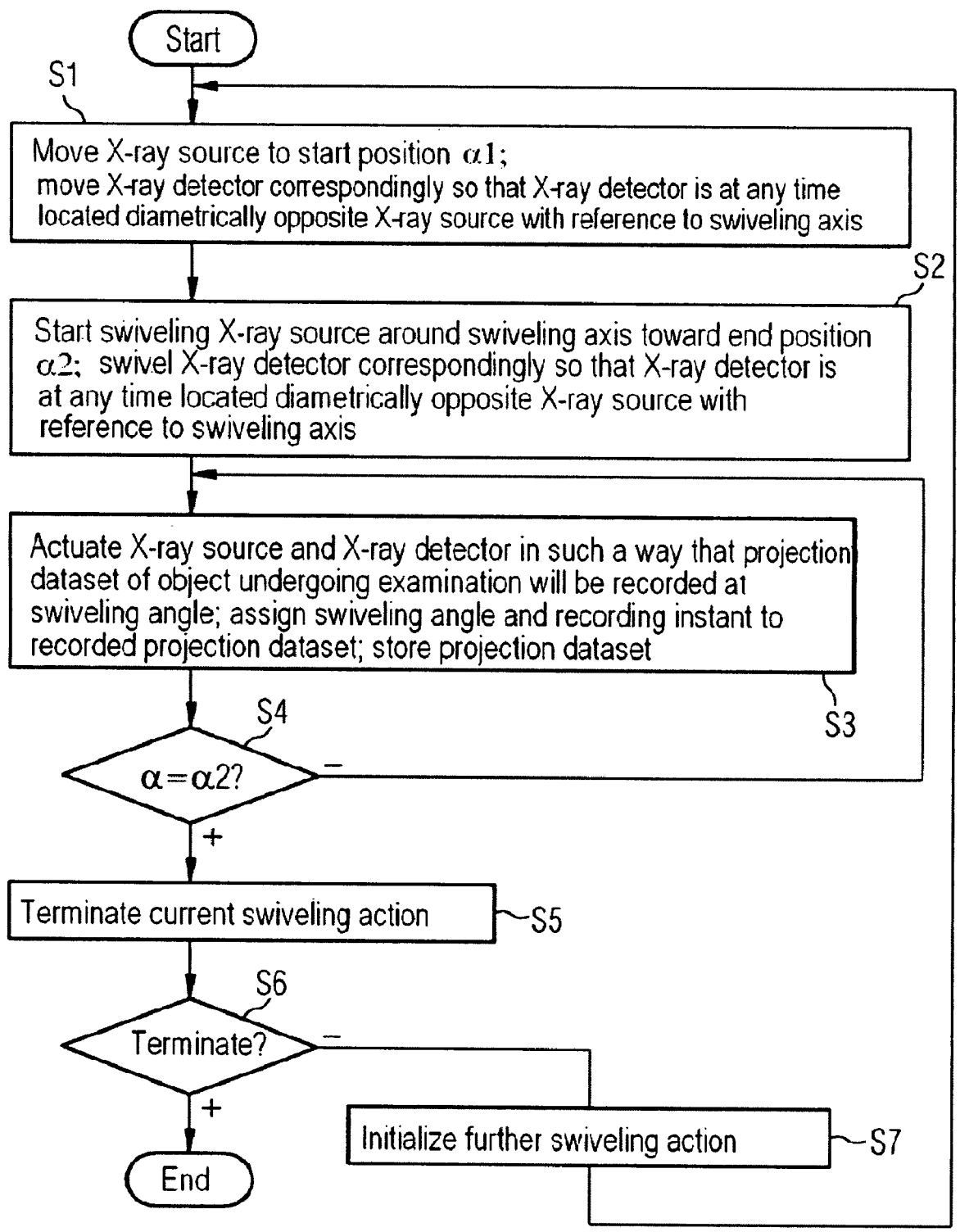
FIG. 2 is a flowchart.

According to FIG. 2, at a step S1 the control device 6 moves the X-ray source 1 to a start position α1 for a first swiveling action. The start position α1 for the first swiveling action can correspond with, for example, a position of the X-ray source 1 that has been drawn as a dashed outline in FIG. 1 and assigned the reference numeral 1'.

At a step S2 the control device 6 begins to swivel the X-ray source 1 around the swiveling axis 4 toward an end position α2. The end position α2 for the first swiveling action can correspond with, for example, a position of the X-ray source 1 that has likewise been drawn as a dashed outline in FIG. 1 and assigned the reference numeral 1".

Swiveling of the X-ray source 1 takes place over an angular range β that is as a rule greater than 180°. In typical embodiments of the X-ray system the angular range β is, for example, 200°, 225°, or 270°. Even an angular range β of 360° will basically be possible if a telescopically extendable C-arm 3 or another type of positioning is used. What is decisive is that the X-ray source 1 is not continuously rotated around the swiveling axis 4 through a large number of revolutions but rather that the swiveling action will be terminated when the end position α2 has been reached.

Swiveling of the X-ray source 1 from its start positional to its end position α2 takes a swiveling time T2. The swiveling time T2 is customarily within a range of several seconds, for example approximately 3 to 5 seconds.

The X-ray detector 2 is swiveled correspondingly while the X-ray source 1 is being swiveled so that the X-ray detector 2 will at any time be located diametrically opposite the X-ray source 1 with reference to the swiveling axis 4. The X-ray source 1 and the X-ray detector 2 are furthermore actuated by the control device 6 during the swiveling action in such a way that in each case one projection dataset P of the object 5 undergoing examination will be recorded at swiveling angles α. For example an angular distance δα between swiveling angles α following in direct succession can be within a range of 0.5° to 5°, in particular 1° to 2°.

The recorded projection datasets P are stored by the control device 6. The control device 6 furthermore assigns each projection dataset P the swiveling angle α at which the projection dataset P was recorded. The control device 6 also assigns each projection dataset P a recording instant t at which the respective projection dataset P was recorded.

The X-ray detector 2 is one-dimensional or two-dimensional. If it is one-dimensional it has according to FIGS. 3 and 4 a number of detector elements 10 in the tangential direction (which is to say in a direction around the swiveling axis 4). A measuring signal on the basis of which a data value of a corresponding data element is determined is recorded by means of each detector element 10. The data elements' data values form in their totality the respective projection dataset P. Each data element of each recorded projection dataset P defines a projection line 11 on the basis of the arrangement of the corresponding detector element 10 together with the swiveling angle α at which the respective projection dataset P was recorded. Some possible projection lines 11 have been drawn by way of example in FIGS. 3 and 4.

Each projection line 11 has been traveled along by a corresponding X-ray beam 12 on its way from the X-ray source 1 to the X-ray detector 2. Some possible X-ray beams 12 have been drawn by way of example in FIGS. 3 and 4.

Figure 3:
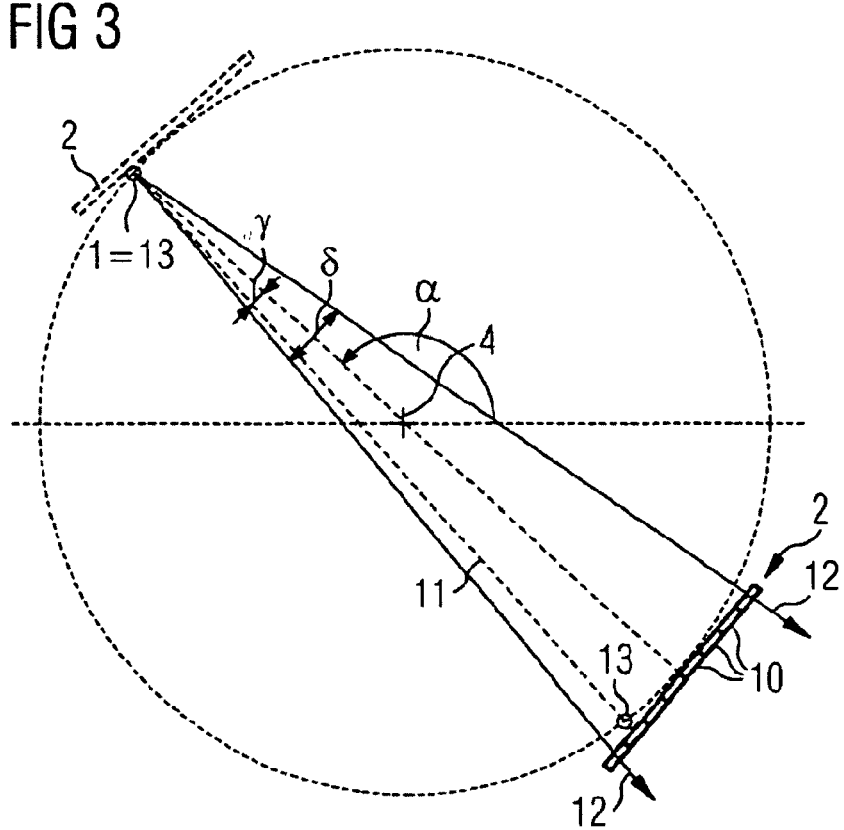
FIGS. 3 and 4 show possible beam paths.
Figure 4:
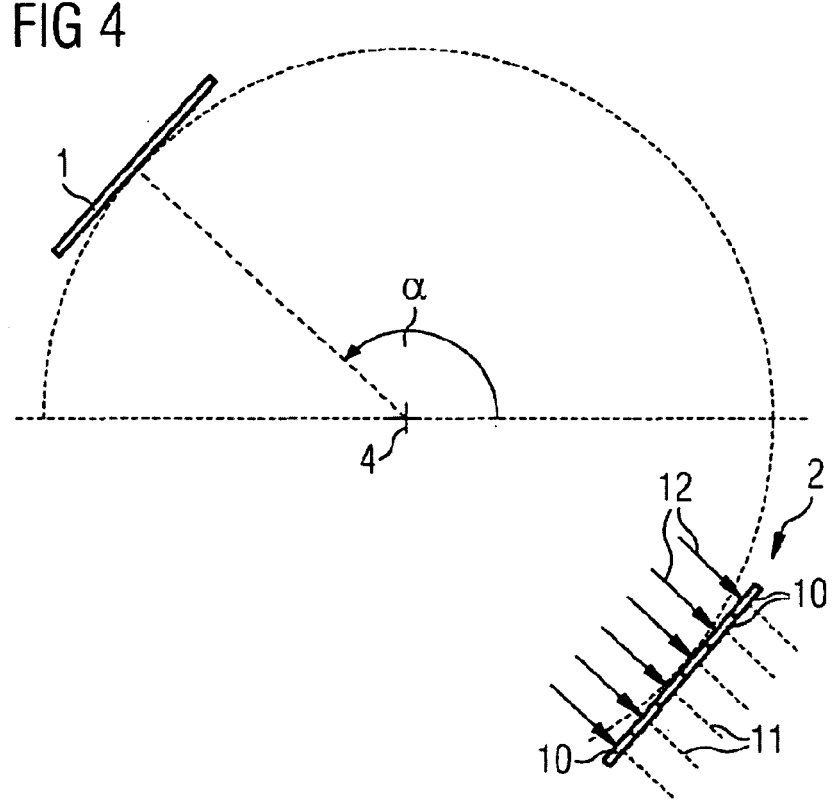

The X-ray source 1 is as a rule—see FIGS. 1 and 3—basically punctiform. In that case the projection lines 11 of each projection dataset P will have a common intersecting point 13 corresponding with the X-ray source 1. In that case the projection datasets P will be perspective projections of the object 5 undergoing examination. It is, though, according to FIG. 4 alternatively possible for the projection lines 11 of the projection datasets P to be oriented parallel to each other within each projection dataset P. In that case the projection datasets P will correspond with parallel projections of the object 5 undergoing examination.

The X-ray detector 2 is as a rule embodied as two-dimensional. The X-ray detector 2 will in that case have a plurality of detector rows, with the detector rows being embodied in the manner described above in conjunction with FIGS. 3 and 4 for the one-dimensional case, and with the detector rows being relative to each other arranged adjacently in the axial direction (which is to say in a direction parallel to the swiveling axis 4).

At a step S4 the control device 6 checks whether the X-ray source 1 has reached its end position α2 yet. Until it has, the control device 6 will keep returning to step S3.

The control device 6 will otherwise terminate the current swiveling action at a step S5. At a step S6 the control device 6 checks whether the acquisition method is to be terminated.

If not, the control device 6 will at a step S7 initiate a further swiveling action. It will then immediately return to step S2.

Possible embodiments of the method shown in FIG. 2 will be explained in more detail later in conjunction with FIGS. 5 and 7. Possible implementations of step S7 will in particular become apparent from said embodiments.

The control device 6 requires a cycle time T to perform steps S2 to S7. The reciprocal of the cycle time T corresponds to a repetition frequency f at which the mutually discrete swiveling actions follow in succession. The cycle time T is specified as being at most half the minimum time constant T1. The repetition frequency f is correspondingly thereto at least twice the reciprocal of the minimum time constant T1.

It can be seen from the above explanations that the X-ray source 1 is swiveled around the swiveling axis 4 during a plurality of mutually discrete swiveling actions. The X-ray detector 2 is swiveled correspondingly during each swiveling action. In each case one of the projection datasets P will furthermore be recorded during each swiveling action at swiveling angles α of the X-ray source 1 and stored.

According to FIGS. 5 and 6 it is possible to embody the acquisition method shown in FIG. 2 as follows:

Steps S1 to S6 are retained. Step S7 is omitted. A return is furthermore made from step S6 not to step S2 but to step S1. Step S7 is thus replaced by step S1.

Figure 5:
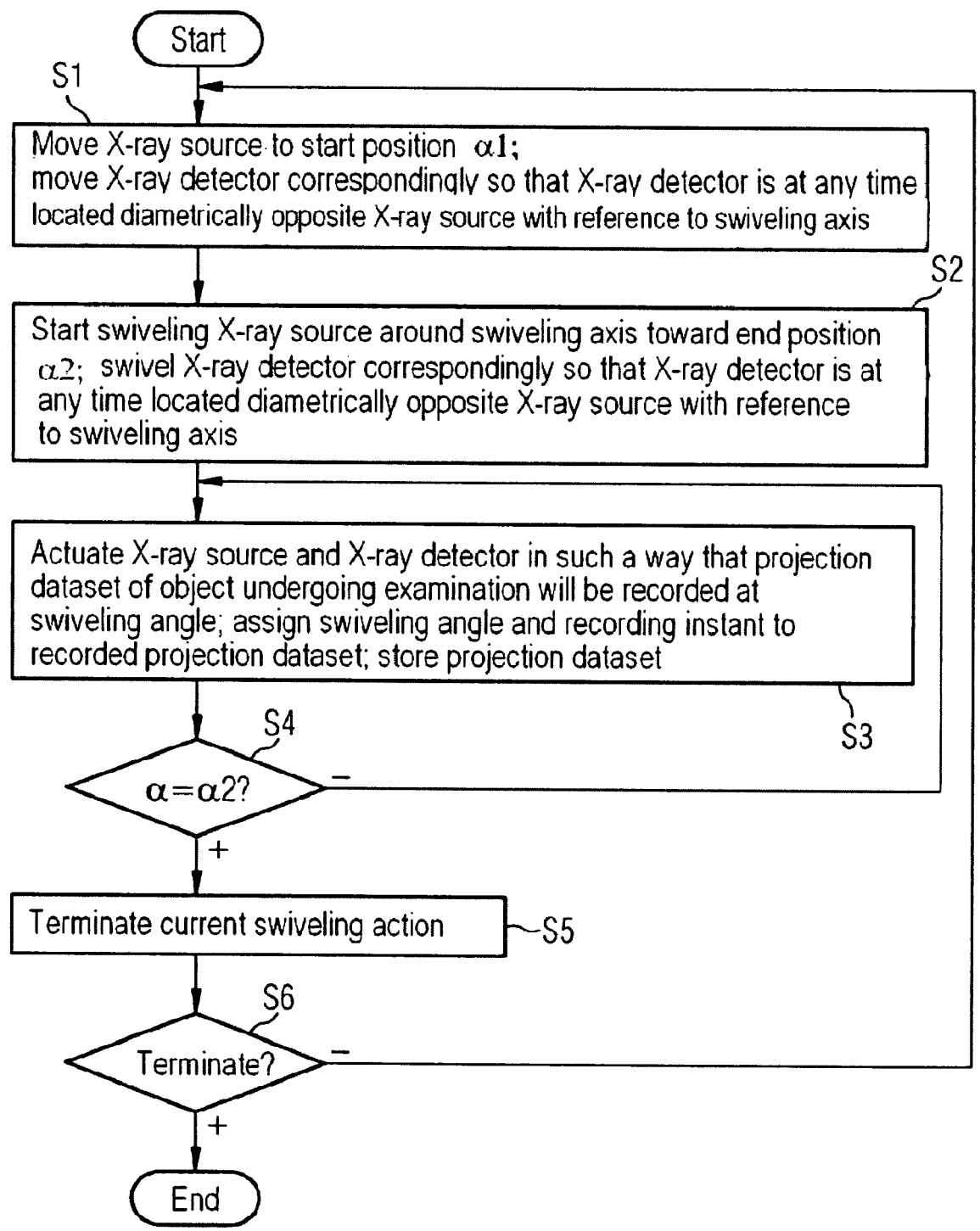
FIG. 5 is a flowchart.

With the procedure according to FIG. 5 the swiveling actions are in the same direction. That is very clearly apparent from FIG. 6. Each swiveling action is furthermore immediately followed by a pause 14 in recording during which no projection datasets P are recorded or stored.

The pauses 14 in recording have a pause duration T3. The pause duration T3 is preferably shorter than the swiveling time T2. For example it can be only half as long or only a third as long as the swiveling time T2. Step S1 is performed during the pauses 14 in recording. During the pauses 14 in recording the X-ray source 1 and X-ray detector 2 are therefore in the case of the procedure shown in FIGS. 5 and 6 transferred from end positions α2 of the preceding swiveling action to start positions α1 of the succeeding swiveling action. Because the X-ray source 1 and X-ray detector 2 must during the pauses 14 in recording be transferred to their start positions α1 for the succeeding swiveling action, the pauses 14 in recording must be present in the case of the procedure according to FIG. 5. So although they can be shortened by appropriately embodying the X-ray system, they cannot be eliminated altogether.

As an alternative to the embodiment according to FIGS. 5 and 6 it is possible according to FIGS. 7 and 8 to modify the procedure shown in FIG. 2 as follows:

According to FIG. 7, step S1 is preceded by a step S8. At step S8 the control device 6 sets the start position α1 to a first end angular position β1 and the end position α2 to a second end angular position β2. Step S7 is present. It is implemented in such a way that the start position α1 and end position α2 will be mutually exchanged.

With the procedure shown in FIG. 7, swiveling actions following in direct succession are oriented in opposite directions. That is particularly clearly apparent from FIG. 8.

With the procedure shown in FIGS. 7 and 8 it is possible for the swiveling actions to follow in succession without interruption. An—at least short—pause 14 in recording is, though, preferably also present in the case of the procedure shown in FIG. 7.

The repetition frequency f at which the swiveling actions follow in succession is as a rule between around 0.2 Hz and around 0.3 Hz. A swiveling action therefore requires—where applicable including a pause 14 in recording—a cycle time T of somewhat above 3 seconds to about 5 seconds. Said numerical values can in individual cases be exceeded or undershot. However, the repetition frequency f ought not to fall below 0.1 Hz. It will as a rule only be possible to exceed 0.5 Hz at considerable cost in terms of equipment.

Regardless of whether the procedure shown in FIGS. 5 and 6 is used or whether the procedure shown in FIGS. 7 and 8 is used, a mean time distance TM between the temporal midpoint of one swiveling action and the temporal midpoint of the immediately following swiveling action will correspond with the cycle time T. The mean time distance TM is thus less than half the minimum time constant T1.

It is also possible for a maximum time distance TM' between the temporally first projection dataset P of one swiveling action and the temporally last projection dataset P of the immediately following swiveling action to be less than half the minimum time constant T1. The maximum time distance TM' can, though, alternatively also be greater than half the minimum time constant T1. The reason therefor will become apparent from the following explanation of the inventive evaluating method by means of which the recorded projection datasets P are evaluated.

Figure 9:
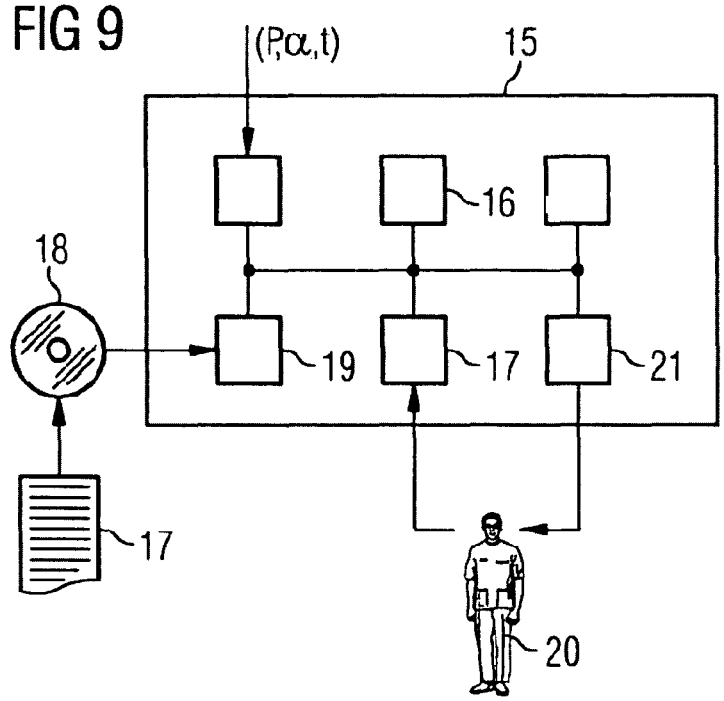
FIG. 9 is a block diagram of a computer.

The projection datasets P are evaluated according to FIGS. 9 and 10 by means of a computer 15 to which the projection datasets P are supplied. The computer 15 can be—see FIG. 9—an autonomous computer. It can alternatively be—see FIG. 10—a constituent part of the X-ray system. If it is a constituent part of the X-ray system it can be—see again FIG. 10—identical to the control device 6 of the X-ray system. The control device 6 of the X-ray system and the computer 15 can alternatively be constituent parts of the X-ray system that are different from each other.

The computer 15 has a bulk storage 16 in which is stored a computer program 17. The computer program 17 is supplied to the computer 15 via a data medium 18 on which the computer program 17 is stored in exclusively machine-readable form. The computer program 17 is loaded into the computer 15 via a suitable interface 19, stored in the bulk storage 16, and executed by the computer 15. The computer program 17 causes the computer 15 to perform an evaluating method for the projection datasets P that were recorded according to the above-described acquisition method. The evaluating method is explained in more detail below in conjunction with FIG. 11.

As already mentioned in conjunction with FIG. 10, the computer 15 can be identical to the control device 6. In that case the computer program 17 will additionally be embodied as a control program 7 and cause the computer 15 to control the X-ray system according to one of the above-described acquisition methods. The acquisition methods having already been explained in detail above, reference can be made to the above explanations in connection with the acquisition methods.

For implementing the evaluating method, according to FIG. 11 the computer 15 accepts the projection datasets P, the corresponding swiveling angle α, and the corresponding recording instants t from the control device 6 at a step S11.

Owing to the way in which the projection datasets P were recorded (see the above explanations relating to FIGS. 5 to 8), the projection datasets P can be combined into recording groups each of which contains the projection datasets P that were recorded during a single swiveling action of the X-ray source 1 around the swiveling axis 4. Within each recording group the swiveling angles α of the respective projection datasets P form a strictly monotonic function of the corresponding recording instants t.

If the swiveling actions were in the same direction (see FIGS. 5 and 6), then the functions will exhibit the same monotony in all recording groups. Owing to the necessary pauses 14 in recording, a minimum time distance TM" between the temporally last projection dataset P of a recording group and the temporally first projection dataset P of the immediately following recording group is greater—for the most part even far greater—than a time distance δt between two projection datasets P in direct succession within the same recording group.

If, while the projection datasets P were being recorded, swiveling actions in direct succession were oriented in opposite directions (see FIGS. 7 and 8), then the functions will change their monotony from one recording group to the temporally immediately following recording group.

It is possible for the computer 15 to determine the recording groups independently at a step S12. Step S12 is, though, only an option. It can be omitted. Because it is optional, step S12 has only been drawn with a dashed border in FIG. 11.

At a step S13 the computer 15 specifies a number of reconstruction times ti. As a minimum the computer 15 specifies a single reconstruction time ti. However, as a rule it specifies a plurality of reconstruction times ti.

It is possible for the computer 15 to specify the reconstruction times ti independently, for example using the recording instants t. The reconstruction times ti can alternatively have been permanently prespecified for the computer 15. It is also possible for the reconstruction times ti to be prespecified for the computer 15 by an operator 20. The operator 20 can be identical to the operator 9. The operator 20 may, though, also be someone else.

At a step S14 the computer 15 selects one of the reconstruction times ti.

At a step S15 the computer 15 determines a reconstruction group of reconstruction datasets for the selected reconstruction time ti using the projection datasets P. Step S15 will be explained in more detail below. It is, though, mentioned now that each reconstruction dataset contains at least one reconstruction data value assigned to a reconstruction line and that the computer 15 determines the reconstruction datasets of each determined reconstruction group in such a way that they refer to the selected reconstruction time ti. The reconstruction time ti is hence uniform for all reconstruction datasets of the respective reconstruction group.

Using, for example, the Feldkamp algorithm (Practical Cone Bean algorithm, JOSA 1, 1984, pages 612-619) generally known to technical specialists, at a step S16 the computer 15 determines a reconstruction of the object 5 undergoing examination on the basis of the reconstruction datasets of the respective reconstruction group.

At a step S17 the computer 15 checks whether it has performed steps S15 and S16 for all reconstruction times ti yet. If not, then the computer 15 will proceed to a step S118. At step S18 the computer 15 selects another, hitherto not selected reconstruction time ti. From step S18 it returns to step S15.

If, conversely, the computer 15 has already determined all reconstructions of the object 5 undergoing examination, then it will proceed to a step S19. At step S19 the computer 15 carries out evaluations of the determined reconstructions. For example it can arrange the reconstructions in a time sequence and feed them out to the operator 20 on a display device 21.

As already mentioned, the computer 15 determines the reconstruction datasets of each reconstruction group in such a way that they relate to the respective reconstruction time ti. According to FIG. 12 the computer 15 can realize that by, for example, determining the corresponding reconstruction data value for each reconstruction dataset using the data elements of the projection datasets P whose projection lines 11 correspond as far as possible with the reconstruction line of the respective reconstruction dataset and using the corresponding recording times t.

The result, therefore, is that the computer 15 determines the reconstruction datasets for fictional recording times, namely the reconstruction times ti. Said determining is possible because the cycle time T is at most half the minimum time constant T1, meaning that recording of the projection datasets P satisfied the sampling theorem.

If the swiveling actions were in the same direction, then all swiveling angles α will be approached with the repetition frequency f. The sampling theorem will therefore clearly have been satisfied for all swiveling angles α. If, conversely, swiveling actions in direct succession were oriented in opposite directions, then a distinction must be made.

If the repetition frequency f is so great—see FIG. 8—that the maximum time distance TM' is also less than half the minimum time constant T1, then the sampling theorem will have been satisfied for all swiveling angles α. If in the case of FIG. 8 the maximum time distance TM' is conversely greater than half the minimum time constant T1, then a further distinction must be made.

In many cases—in particular if the cycle time T is only slightly less than half the minimum time constant T1 and the angular range β traversed by the X-ray source 1 is only slightly greater than a minimum angular range necessary for applying the reconstruction algorithm employed at step S16—then either it will not be possible to determine the reconstruction datasets or the errors possibly occurring while the reconstruction datasets are being determined and the artifacts associated therewith will have to be accepted. Conversely, it can in other cases be possible to satisfy the sampling theorem although the maximum time distance TM' is greater than half the minimum time constant T1. That is explained in more detail below with the aid of FIG. 8 in conjunction with a numerical example.

It is initially assumed below that although the cycle time T is greater than a fourth the minimum time constant T1 it is still much less than half the minimum time constant T1. It is assumed by way of example that the cycle time T is one third the minimum time constant T1.

It is further assumed—purely by way of example—that the swiveling time T2 is three seconds and that between the swiveling actions there is a pause 14 in recording having a pause duration T3 of one second. It is further assumed that the angular range β through which the X-ray source 1 is swiveled is 240° and that the swiveling action is even. It is further assumed, with no further limitations on generality, that the traversed angular range β extends from 0° to 240°, meaning that even sampling therefore takes place at 120'.

According to the above numerical example the cycle time T is hence four seconds and the minimum time constant T1 12 seconds. Sampling after in each case six seconds would hence just be adequate.

By simply employing the above numerical values it can immediately be calculated that sampling will take place with a sampling interval δT of six seconds or less for swiveling angles α between 40° and 200°. The sampling theorem will hence be satisfied in a thus defined mid angular range.

Outside the mid angular range, meaning at swiveling angles α of 0° to 40° and 200° to 240°, the sampling theorem will indeed be violated if only a single projection dataset P is used for each recording group. Said violating will for one thing be only slight in terms both of the necessary angular range (many reconstruction algorithms require only projection datasets P that in total extend across an angular range of 180° plus an opening angle δ formed by the X-ray detector 2 with the X-ray source 1) and of the maximum interval between two samplings, so that any artifacts are likely to be only small in scale.

It is, though, above all possible to exploit the fact that complementary beam paths exist particularly in outer angular ranges extending, according to the above numerical example, from 0° to 60° and from 180° to 240°. Especially in the case of parallel projections, projection datasets P whose swiveling angles α are mutually displaced by 180° are mutually complementary. Similar statements apply—see the position drawn additionally in dashed-line form of the intersecting point 13 and the X-ray detector 2 in FIG. 3—in the case of perspective projections. In that case additional account must, however, be taken of a beam angle γ—see FIG. 3—formed by the respective projection line 11, having a straight line through the X-ray source 1, and the swiveling axis 4. What must also be taken into account is that in the case of beam angles γ not lying within the swiveling plane of the X-ray source 1 a slight though for the most part tolerable error will occur. That is also why the formulation "as far as possible" has been used.

The corresponding procedures for determining the complementary beam paths are known to technical experts as "rebinning". Reference is made by way of example to "3D cone beam CT reconstruction for circular trajectories" by M. Grass, T. Köhler, and R. Proska, published in Physics in Medicine and Biology, vol. 45, 2000, pages 329-347.

According to the above numerical example, projection datasets P assigned swiveling angles α between 0° and 60° correspond with projection datasets P assigned swiveling angles α between 180° and 240°. In the case of parallel projections, according to the above numerical example the mid angular range and outer angular ranges overlap. Sufficiently frequent effective sampling can thus be ensured for each swiveling angle α. That is possible in the case of perspective projections if the opening angle δ does not become too large. Even if the sampling theorem cannot be satisfied for all projection lines 11 owing to the use of complementary beam paths, the number of projection lines 11 for which the sampling theorem has not been satisfied can at least be reduced.

Figure 13:
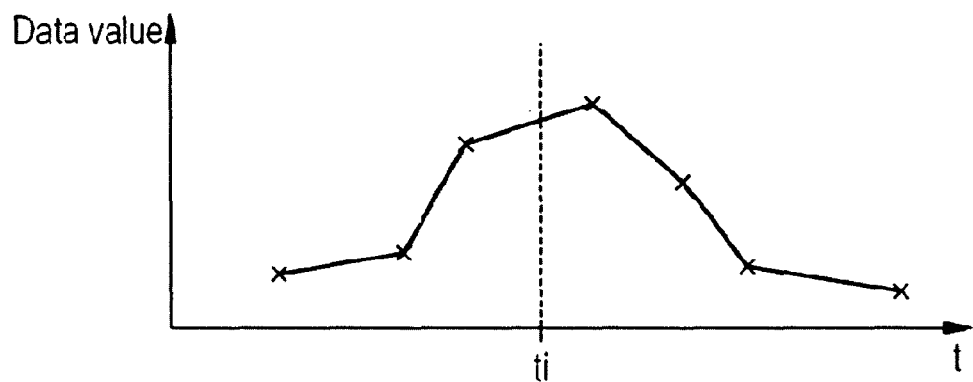
FIGS. 13 and 14 are time charts.
Figure 14:
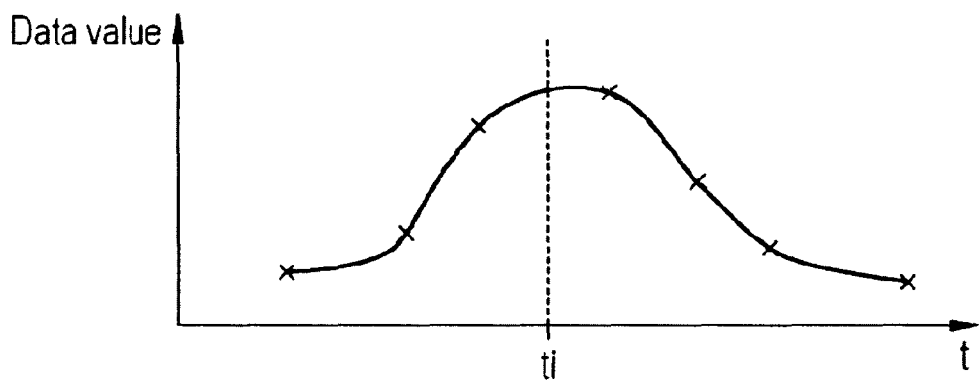

For determining the reconstruction data values with reference to each reconstruction dataset, the computer 15 preferably uses only data elements whose recording instants t are close to the respective reconstruction time ti. According to FIG. 13, with reference to mutually corresponding projection lines 11 it is, for example, possible to perform a linear interpolation of temporally adjacent data elements. It is alternatively possible according to FIG. 14 to link the corresponding data values together by means of smooth curves. In particular splines, for example B-splines, are possible smooth curves.

It is possible for the computer 15 to determine the reconstruction data values within the scope of step S15 using individual reconstruction lines. That will be explained in more detail below in conjunction with FIG. 15.

Figure 15:
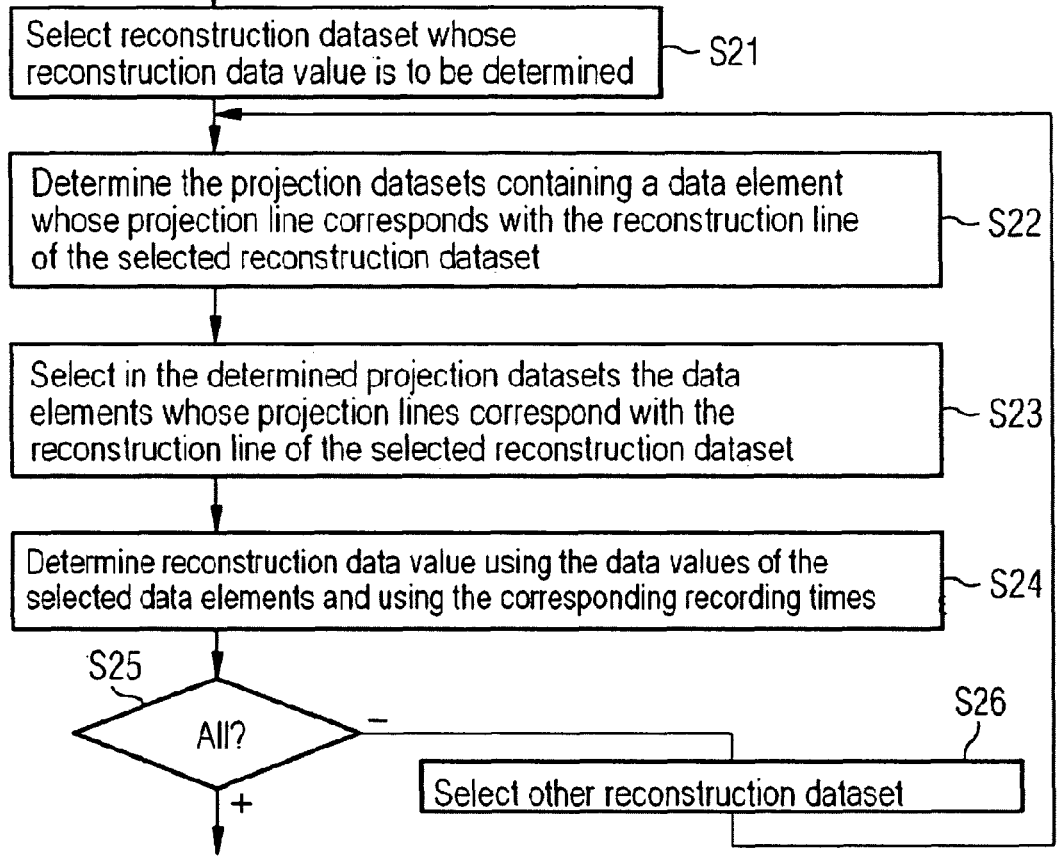

According to FIG. 15, at a step S21 the computer 15 selects a reconstruction dataset whose reconstruction data value is to be determined.

At a step S22 the computer 15 determines the projection datasets P containing a data element whose projection line 11 corresponds as far as possible with the reconstruction line of the selected reconstruction dataset.

At a step S23 the computer 15 selects the corresponding projection lines 11 in the projection datasets P determined at step S22.

At a step S24 the computer 15 determines the reconstruction data value using the data values of the data elements assigned to the projection lines 11 selected at step S23 and using the corresponding recording times t.

At a step S25 the computer 15 checks whether it has performed steps S22 to S24 for all reconstruction datasets yet. If not, then at a step S26 the computer 15 will select another reconstruction dataset of the respective reconstruction group and return to step S22.

The procedure shown in FIG. 15 can always be carried out. It will be expedient to implement it particularly when the projection datasets P correspond with perspective projections and the mid angular range is relatively small.

Figure 16:
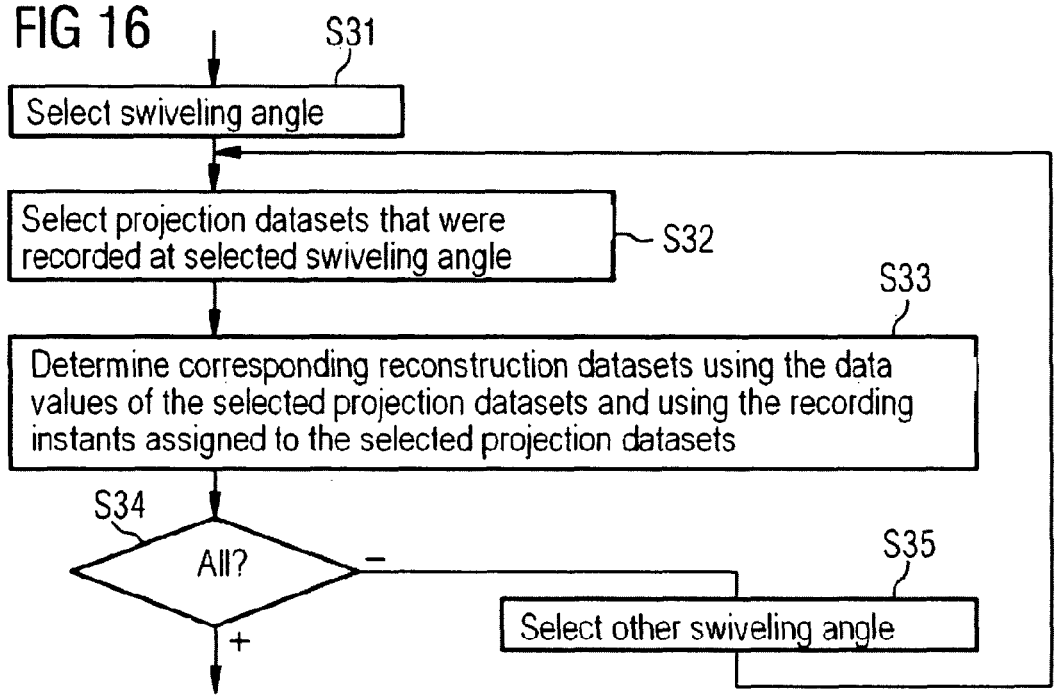

Particularly when the sampling theorem has been satisfied projection by projection (whether because the cycle time T is sufficiently short, or because the projection datasets P correspond with parallel projections and overlapping occurs between the outer angular ranges and mid angular range, or because the swiveling actions are all oriented in the same direction), a procedure that will be explained in more detail below in conjunction with FIG. 16 is available as an alternative to FIG. 15.

According to FIG. 16, at a step S31 the computer 15 initially selects a swiveling angle α.

At a step S32 the computer 15 selects the projection datasets P that were recorded at the selected swiveling angle α.

At a step S33 the computer 15 determines corresponding reconstruction datasets using the data values of the data elements of the selected projection datasets P and using the recording instants t assigned to the selected projection datasets P.

At a step S34 the computer 15 checks whether it has performed steps S32 and S33 for all necessary swiveling angles α yet. If not, then at a step S35 the computer 15 will select another swiveling angle α and return to step S32.

According to FIG. 17 it is possible to combine the procedures shown in FIGS. 15 and 16. Said procedure is expedient particularly in the case of perspective projections when the mid angular range is relatively large.

Both steps S31 to S35 and steps S21 to S26 occur in FIG. 17. Said steps have already been explained above in conjunction with FIGS. 15 and 16. Reference is therefore made to the above explanations.

According to FIG. 17, a step S36 comes after step S32. At step S36 the computer 15 checks whether with reference to the selected swiveling angle α a maximum sampling interval δT of the projection datasets P selected at step S32 is less than half the minimum time constant T1. Step S33 will be performed only if that condition has been met. A step S37 will otherwise be performed at which the computer 15 registers the projection lines 11 assigned to the selected swiveling angle α as the reconstruction lines.

Steps S21 to S26 are performed in the same way as described above in conjunction with FIG. 15. It needs only to be taken into account that only the reconstruction lines that were registered within the scope of step S37 can be selected within the scope of steps S21 to S26 shown in FIG. 17.

The procedure shown in FIG. 17 causes the computer 15 to determine the reconstruction data values as far as possible by swiveling angles and only secondarily by reconstruction lines.

The recording of time series by means of C-arm X-ray systems is made possible for the first time by the present invention. The present invention constitutes a major advance because it enables time series to be recorded and displayed in the interventional clinical sphere.

The above description serves solely to explain the present invention. The scope of protection for the present invention is by contrast determined solely by the attached claims.

The invention claimed is:

1. A method for evaluating a plurality of projection datasets of an object under a medical examination, comprising:
   assigning a plurality of recording instants to the projection datasets at which the projection datasets are recorded by an X-ray detector located diametrically opposite to an X-ray source with reference to a swiveling axis;
   assigning a plurality of swiveling angles to the projection datasets at which the X-ray source is swiveled with reference to the swiveling axis at the recording instants;
   determining an end position;
   terminating swiveling the X-ray source when the end position has been reached;
   defining a plurality of projection lines for data elements of the projection datasets along which X-ray beams travel from the X-ray source to the X-ray detector;
   selecting a reconstruction time;
   determining reconstruction datasets from the projection datasets for the selected reconstruction time so that the reconstruction time is uniform for all the reconstruction datasets;
   assigning reconstruction lines to reconstruction data values of the reconstruction datasets;
   determining the reconstruction data values by a temporal interpolation using the data elements whose projection lines correspond with the reconstruction lines and using the recording instants; and
   reconstructing the object based on the reconstruction data values of the reconstruction datasets having the uniform reconstruction time for medically examining the object.

2. The method as claimed in claim 1, wherein a plurality of recording groups are formed each comprising projection datasets that are recorded in a single swiveling action of the X-ray source around the swiveling axis.

3. The method as claimed in claim 2, wherein the swiveling angles of the projection datasets have a monotonic function with the corresponding recording instants in each same recording group.

4. The method as claimed in claim 2,
   wherein the swiveling angles of the projection datasets have monotonic functions with the corresponding recording instants in all the recording groups,
   wherein the monotonic functions have a same monotony in recording groups recorded in an identical direction of swiveling actions, and
   wherein a time distance between a temporally last projection dataset of a recording group and a temporally first projection dataset of an immediately following recording group is greater than a time distance between two directly successive projection datasets within a same recording group.

5. The method as claimed in claim 2,
   wherein the swiveling angles of the projection datasets have monotonic functions with the corresponding recording instants in all the recording groups, and
   wherein the monotonic functions change monotony from a recording group to a temporally immediately following recording group recorded in an opposite direction of swiveling actions.

6. The method as claimed in claim 2, wherein the recording groups are determined by a computer.

7. The method as claimed in claim 1, wherein the projection lines are parallel to each other.

8. The method as claimed in claim 1, wherein the projection lines comprises a common intersecting point.

9. The method as claimed in claim 1, wherein the reconstruction data values are temporally interpolated using the data elements whose recording instants bracket the reconstruction time.

10. The method as claimed in claim 1, wherein a weighting factor defining an extent to which the data elements of the projection lines contribute to corresponding reconstruction data values is determined by the reconstruction lines.

11. The method as claimed in claim 1, wherein a weighting factor defining an extent to which the data elements of the projection lines contribute to corresponding reconstruction data values is determined by the swiveling angles.

12. The method as claimed in claim 1, wherein a weighting factor defining an extent to which the data elements of the projection lines contribute to corresponding reconstruction data values is determined by the swiveling angles and by the reconstruction lines.

13. A non-transitory computer readable medium encoded with a computer program which when implemented on a computer configures the computer to perform evaluating a plurality of projection datasets of an object under a medical examination, wherein the computer program is configured to:
   assign a plurality of recording instants to the projection datasets at which the projection datasets are recorded by an X-ray detector located diametrically opposite to an X-ray source with reference to a swiveling axis,
   assign a plurality of swiveling angles to the projection datasets at which the X-ray source is swiveled with reference to the swiveling axis at the recording instants,
   determine an end position,
   terminate swiveling the X-ray source when the end position has been reached,
   define a plurality of projection lines for data elements of the projection datasets along which X-ray beams travel from the X-ray source to the X-ray detector,
   select a reconstruction time,
   determining reconstruction datasets from the projection datasets for the selected reconstruction time so that the reconstruction time is uniform for all the reconstruction datasets,
   assign reconstruction lines to reconstruction data values of the reconstruction datasets,
   determine the reconstruction data values by a temporal interpolation using the data elements whose projection lines correspond with the reconstruction lines and using the recording instants, and
   reconstruct the object based on the reconstruction data values of the reconstruction datasets having the uniform reconstruction time for medically examining the object.

14. The non-transitory computer readable medium as claimed in claim 13, wherein a plurality of recording groups are formed each comprising projection datasets that are recorded in a single swiveling action of the X-ray source around the swiveling axis.

15. The non-transitory computer readable medium as claimed in claim 14, wherein the recording groups are determined by the computer program.

16. The non-transitory computer readable medium as claimed in claim 13, wherein the computer program is further configured to control the X-ray source and the X-ray detector for recording the projection datasets during a plurality of discrete swiveling actions.

17. An X-ray system for performing a medical examination of an object, comprising:
   an X-ray source that emits X-ray beams to the object;

an X-ray detector located diametrically opposite to the X-ray source with reference to a swiveling axis that records a plurality of projection datasets of the object by detecting the X-ray beams penetrating the object; and a computer that:
- assigns a plurality of recording instants to the projection datasets at which the projection datasets are recorded,
- assigns a plurality of swiveling angles to the projection datasets at which the X-ray source is swiveled with reference to the swiveling axis at the recording instants,
- determines an end position,
- terminates swiveling the X-ray source when the end position has been reached,
- defines a plurality of projection lines for data elements of the projection datasets along which the X-ray beams travel from the X-ray source to the X-ray detector,
- selects a reconstruction time,
- determines reconstruction datasets from the projection datasets for the selected reconstruction time so that the reconstruction time is uniform for all the reconstruction datasets,
- assigns reconstruction lines to reconstruction data values of the reconstruction datasets,
- determines the reconstruction data values by a temporal interpolation using the data elements whose projection lines correspond with the reconstruction lines and using the recording instants, and
- reconstructs the object based on the reconstruction data values of the reconstruction datasets having the uniform reconstruction time for medically examining the object.

18. The X-ray system as claimed in claim 17, wherein a plurality of recording groups are formed each comprising projection datasets that are recorded in a single swiveling action of the X-ray source around the swiveling axis.

19. The X-ray system as claimed in claim 18, wherein the recording groups are determined by the computer.

20. The X-ray system as claimed in claim 17, wherein the computer controls the X-ray source and the X-ray detector for recording the projection datasets during a plurality of discrete swiveling actions.

* * * * *